United States Patent
Nazarov et al.

(10) Patent No.: US 7,160,485 B2
(45) Date of Patent: *Jan. 9, 2007

(54) LYOTROPIC LIQUID CRYSTAL SYSTEMS BASED ON PERYLENETETRACARBOXYLIC ACID DIBENZIMIDAZOLE SULFODERIVATIVES, RELATED ANISOTROPIC FILMS, AND METHODS FOR MAKING

(75) Inventors: Victor V. Nazarov, Moscow (RU); Elena N. Sidorenko, Moscow (RU)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/714,057

(22) Filed: Nov. 14, 2003

(65) Prior Publication Data

US 2004/0215015 A1   Oct. 28, 2004

Related U.S. Application Data

(60) Provisional application No. 60/465,657, filed on Apr. 25, 2003.

(51) Int. Cl.
| | |
|---|---|
| C09K 19/52 | (2006.01) |
| C09K 19/54 | (2006.01) |
| G02B 5/30 | (2006.01) |
| C07D 235/04 | (2006.01) |
| C07D 403/10 | (2006.01) |
| C07D 471/02 | (2006.01) |

(52) U.S. Cl. .............................. 252/299.01; 252/299.1; 428/1.1; 428/1.31; 548/304.4; 548/301.7; 548/313.7; 548/314.4

(58) Field of Classification Search ................ 428/1.1, 428/1.31; 252/299.01, 299.1; 548/301.7, 548/313.7, 314.4, 304.4
See application file for complete search history.

(56) References Cited

U.S. PATENT DOCUMENTS

| | | | |
|---|---|---|---|
| 2,553,961 A | 5/1951 | Dreyer | |
| 5,739,296 A | 4/1998 | Gvon et al. | |
| 6,174,394 B1 * | 1/2001 | Gvon et al. | ............... 156/100 |
| 6,583,284 B1 * | 6/2003 | Sidorenko et al. | ........... 544/342 |
| 7,025,900 B1 * | 4/2006 | Sidorenko et al. | ...... 252/299.01 |
| 2005/0001202 A1 * | 1/2005 | Sidorenko et al. | ...... 252/299.61 |

FOREIGN PATENT DOCUMENTS

| | | |
|---|---|---|
| EP | 0961138 A1 | 1/1999 |
| EP | 1128192 A1 | 8/2001 |
| WO | US94/05493 | 12/1994 |
| WO | US02/03800 | 8/2002 |

OTHER PUBLICATIONS

B. Bahadur, "Liquid Crystals: Applications and Uses", World Scientific, Singapore New York (1990), vol. 1, p. 101.
J. Lydon, "Chapter XVIII Chromonics", in: Handbook of Liquid Crystals, Wiley—VCH, Weinheim, 1998, vol. 2B, pp. 981-1007.
R.A. Cormier, B.A. Gregg, "Self-Organization in Thin Films of Liquid Crystalline Perylene Diimides" J. Phys. Chem. 101(51), 1997, pp. 11004-11006.

(Continued)

*Primary Examiner*—Shean C. Wu
(74) *Attorney, Agent, or Firm*—Dorsey & Whitney LLP

(57) ABSTRACT

Sulfoderivatives of perylenetetracarboxylic acid dibenzimidazole are provided. These compounds form liquid crystal systems possessing high quality optical properties. The resulting liquid crystal systems are readily applicable onto a substrate to obtain optically isotropic or anisotropic, at least partially crystalline films applicable in various fields.

25 Claims, 3 Drawing Sheets

OTHER PUBLICATIONS

H. Quante, H.Y. Geerts, K. Mullen, "Synthesis of Soluble Perylenebisamidine Deriviatives. Novel Long-Wavelength Absorbing and Fluorescent Dyes", Chem. Mater. 6(2), 1997, pp. 495-500.

Isaac K. Iverson, Sean M. Casey, Wonewoo Seo, Suk-Wah Tam-Chang, "Controlling Molecular Orientation in Solid Films via Self-Organization in the Liquid-Crystalline Phase", American Chemical Society, Jan. 25, 2002, 7 pages.

T. Fiske, L. Ignato, P. Lazarev, V. Nazarov, M. Paukshto, "Molecular Alignment in Crystal Polarizers and Retarders", Society for Information Display, Int. Symp. Digest of Technical Papers, Boston, MA, May 19-24, 2002, pp. 566-569.

V. Nazarov, L. Ignatov, K. Kienskaya, "Electronic Spectra of Aqueous Solutions and Films Made of Liquid Crystal Ink for Thin Film Polarizers", Mol. Mater. 14(2), 2001, pp. 153-163.

Y. Bobrov, L. Blinov, L. Ignatov, G. King, V. Lazarev, Y.D. Ma, V. Nazarov, E. Neburchilova, N. Ovchinnikova, S. Remizov, "Environmental and Optical Testing of Optiva Thin Crystal Film™ Polarizers", Proceedings of the 10th SID Symposium "Advanced display technologies", Minsk, Republic of Belarus, Sep. 18-21, 2001, pp. 23-30.

* cited by examiner

LYOTROPIC LIQUID CRYSTAL SYSTEMS BASED ON PERYLENETETRACARBOXYLIC ACID DIBENZIMIDAZOLE SULFODERIVATIVES, RELATED ANISOTROPIC FILMS, AND METHODS FOR MAKING

RELATED APPLICATIONS

This application claims priority to U.S. Provisional Application Ser. No. 60/465,657, filed on Apr. 25, 2003, the disclosure of which is incorporated by reference in its entirety.

FIELD OF THE INVENTION

The present invention relates generally to the fields of organic chemistry and optically anisotropic coatings. More specifically, the present invention relates to lyotropic liquid crystal systems based on heterocyclic sulfoderivative compounds and methods for manufacturing optically anisotropic coatings based on these compounds.

BACKGROUND OF THE INVENTION

Optical elements are increasingly based on new materials possessing specific, precisely controllable properties. In particular, a necessary element in modern visual display systems is an optically anisotropic film with a combination of optical and other characteristics that may be optimized to suit the requirements of a particular device.

Various polymeric materials have been used in the manufacture of optically anisotropic films. Films based on such materials may acquire anisotropic optical properties through uniaxial extension and modification with organic dyes or iodine. In many applications, the base polymer is polyvinyl alcohol (PVA). Such films are described in greater detail in the monograph *Liquid Crystals: Applications and Uses*, B. Bahadur (ed.), World Scientific, Singapore—N.Y. (1990), Vol. 1, p. 101. However, the low thermal stability of PVA-based films typically limits their application. Development of new materials and methods for the synthesis of optically anisotropic films possessing improved characteristics is therefore quite advantageous. In particular, higher heat resistance, more convenient synthesis, and better film-forming properties are highly desirable.

Organic dichroic dyes have gained prominence in the manufacture of optically anisotropic films with improved optical and working characteristics. Films based on these compounds may be obtained through application of a layer of a liquid crystal (LC) aqueous dye solution containing supramolecules composed of dye molecules onto a substrate surface followed by evaporation of the solvent (e.g. water). The resulting LC films acquire anisotropic properties either through preliminary mechanical ordering of the underlying substrate surface as described, for example, in U.S. Pat. No. 2,553,961 or through subsequent application of external mechanical, electromagnetic or other orienting forces to the LC coating on the substrate as described, for example, in PCT Publication No. WO 94/28073.

Investigations into the application of LC dyes as described above, as well as the properties of related systems have become more extensive in the past decade. Recent studies into these phenomena have been motivated largely by industrial applications in liquid crystal displays (LCDs) and glazing. Dye supramolecules may form lyotropic liquid crystal (LLC) phases. In such phases, dye molecules pack into supramolecular complexes that are shaped generally like columns, which are the basic structural units of a mesophase. High ordering of dye molecules in the columns allows such mesophases to be used for obtaining oriented films characterized by a strong dichroism.

Dye molecules that form supramolecular LC mesophases typically include peripheral groups that render the dyes water-soluble. The mesophases of organic dyes are characterized by specific structures, phase diagrams, optical properties, and dissolving capabilities, as described for example in J. Lydon, Chromonics, in: *Handbook of Liquid Crystals* (Wiley—VCH, Weinheim, 1998), Vol. 2B, pp. 981 to 1007.

Using dichroic dyes capable of forming LLC systems, it is possible to obtain films possessing a high degree of optical anisotropy. Such films exhibit the properties of E-type polarizers, which are related to peculiarities of the optical absorption of supramolecular complexes, and behave as retarders (phase-shifting devices) in the spectral regions where the absorption is insignificant. The phase-retarding properties of these anisotropic films are related to their birefringence (double refraction), that is, a difference in refractive indices measured in the direction of application of the LLC solution onto a substrate and in the perpendicular direction. Films formed from LLC systems based on strong (light-fast) dye molecules are characterized by high thermal stability and light resistance.

The above properties of LLC systems account for the growing interest in these materials. Methods have been developed for preparing films based on such organic dyes. Recent improvements have involved both optimization of the film application conditions and identification of new LLC systems. In particular, new LLC compositions for the synthesis of optically anisotropic films may be obtained by introducing modifiers, stabilizers, surfactants, and other additives to known dyes so as to improve characteristics of the films as described in, for example, published PCT Publication No. WO 94/28073.

In recent years, there has been increasing demand for the films possessing high optical anisotropy that are also characterized by improved selectivity in various wavelength ranges. Films whose absorption maxima occur at different locations in the wide spectral range from the infrared (IR) to the ultraviolet (UV) are very desirable. A broad assortment of compounds capable of forming LLC phases and films possessing the required properties have been developed. However, the number of dyes known to form stable lyotropic mesophases is still relatively small.

Disulfoderivatives of various organic dyes, including perylenetetracarboxylic acid (PTCA) dibenzimidazole (DBI) are important water-soluble dichroic dyes capable of forming stable LLC phases. PCTA DBI species applicable in the manufacturing of optically anisotropic films have been described previously in PCT Publication No. WO 94/28073. In general, PTCA dibenzimidazoles and diimides are characterized by excellent chemical, thermal, and photochemical stability. These properties have triggered increased interest in these substances as potential materials for obtaining optically anisotropic films for LCDs and other optical devices.

Widespread use of these dyes has been hindered by their generally poor solubility in water as well as in some organic solvents. To provide for the solubility of perylene dyes in organic solvents, the introduction of various substituents into the initial molecules has been suggested. Examples of such substituents include oxyethyl groups as described in R. A. Cormier and B. A. Gregg, *Phys. Chem.* 101 (51), 11004 to 11006 (1997) and phenoxy groups as described in H. Quante H. Y. Geerts, and K. Mullen, *Chem. Mater.* 6(2), 495 to 500 (1997). Improved solubility of perylene dyes may also be provided by amino groups as described in I. K. Iverson, S. M. Casey, W. Seo, and S.-W. Tam-Chang, *Langmuir* 18(9), 3510 to 5316 (2002) and by sulfonic groups as described in PCT Publication No. WO 94/28073. The best results to date have been obtained using sulfonic substituent groups, which provide for sufficient solubility and the formation of a stable LLC phase of perylene dyes.

The standard procedure for synthesizing disulfoderivatives is as follows. Controlled amounts of PTCA DBI and oleum are added to a volume of chlorosulfonic acid. Upon termination of the reaction, the mixture is colored and diluted with water. The precipitate is filtered, washed with hydrochloric acid, and dried. This yields water-soluble dibenzimidazole perylenetetracarboxydisulfonic acid, which is dissolved in water and purified. An analysis of the system texture reveals that, beginning with a certain dye concentration, a stable hexagonal lyotropic mesophase is formed in a given temperature interval. Accordingly, a nematic phase is observed within a sufficiently narrow range of dye concentrations and temperatures. The boundaries of existence of isotropic phases, as well as two-phase transition regions, have been determined in this system.

Various dye compositions (also referred to as "inks") used in the manufacture of polarizer films based on PTCA DBI sulfoderivatives have been patented. One example of currently available dyes has the structural formula:

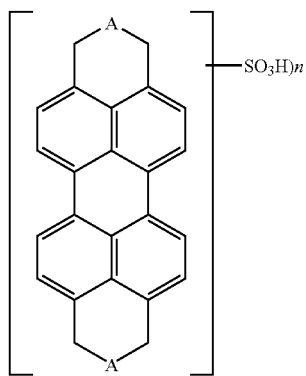

n = 2 or 3 where

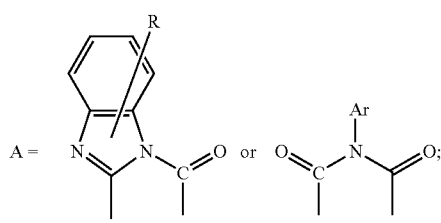

R is H, alkyl group, halogen or alkoxy group; and Ar is substituted or unsubstituted aryl radical. This compound, described in U.S. Pat. No. 5,739,296, selectively absorbs in the spectral region of approximately 550 to 600 nm.

Another currently available dye composition is based on PTCA DBI of the formula

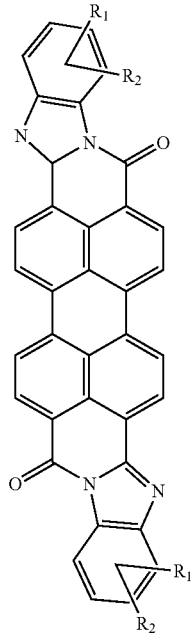

where $R_1$ is H, 3(4)-$CH_3$, 3(4)-$C_2H_5$, 3(4)-Cl, or 3(4)-Br and $R_2$ is 4(5)-$SO_3H$. This compound, described in SU Pat. No. 1,598,430, selectively absorbs in the region of approximately 550 to 600 nm.

LC blends of PTCA DBI sulfoderivatives with various modifying additives introduced to improve the characteristics of anisotropic films were described in PCT Publication No. WO 94/28073. One such compound has the general formula:

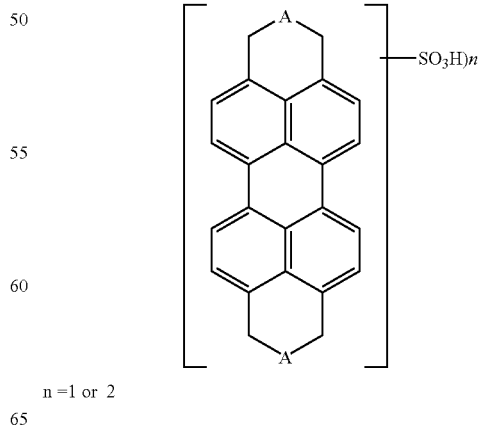

n = 1 or 2 where

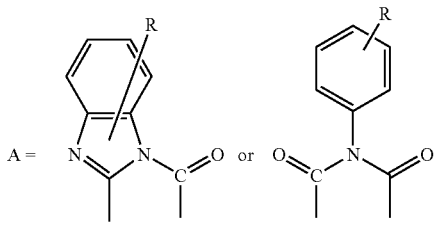

and R is H, Br, Cl, OH, Alk, or Oalk.

Indanthrone disulfoderivatives with various substituents and compositions with various organic cations have been described previously. Thin anisotropic films obtained using LLC systems based on sulfoderivatives of various organic dyes, including perylene dyes, have also been characterized with respect to their properties and structures. In particular, the properties of films obtained using perylene dye-based LLC systems were studied by I. K. Iverson, S. M. Casey, W. Seo, and S.-W. Tam-Chang in Controlling Molecular Orientation in Solid-Crystalline Phase, *Langmuir* 18(9), 3510 to 3516 (2002). All of the studied films were reported to possess a high degree of optical anisotropy.

The properties of thin anisotropic films obtained using LLC systems based on sulfoderivatives of organic dyes of the proposed method were reported in T. Fiske, L. Ignatov, P. Lazarev, V. Nazarov, M. Paukshto Molecular Alignment in Crystal Polarizers and Retarders, *Society for Information Display, Int. Symp. Digest of Technical Papers* (Boston, Mass., May 19–24, 2002), p. 566 to 569. It was established that these films possess at least partially crystalline structures. Optically anisotropic films may be formed on glass, plastic, or other substrate materials. The Violet dye used for the formation of these anisotropic films represents a blend of cis and trans isomers as described in V. Nazarov, L. Ignatov, K. Kienskaya, Electronic Spectra of Aqueous Solutions and Films Made of Liquid Crystal Ink for Thin Film Polarizers, *Mol. Mater.* 14(2), 153 to 163 (2001). Because they exhibit high quality optical characteristics and have dichroic ratios that approach the range of approximately 25 to 30, these films may be used as polarizers as described by Y. Bobrov, L. Blinov, L. Ignatov, G. King, V. Lazarev, Y.-D. Ma, V. Nazarov, E. Neburchilova, N. Ovchinnikova, S. Remizov, Environmental and Optical Testing of Optiva Thin Crystal Film™ Polarizers, *Proceedings of the 10$^{th}$ SID Symposium "Advanced display technologies"*, (Minsk, Republic of Belarus, Sep. 18–21, 2001), p. 23 to 30. Methods for the preparation of such films, including those with high degree of crystallinity, are described in PCT Publication No. WO 02/063,660. Thus, the aforementioned PTCA DBI sulfoderivatives are capable of forming LLC phases. Anisotropic films obtained using this LLC system possess excellent optical characteristics and exhibit good performance as polarizers.

A disadvantage of previously described water-soluble PTCA DBI sulfoderivatives is the difficulty of obtaining related anisotropic films possessing reproducible—for example from batch to batch and on different substrates in the same batch—and homogeneous—over the substrate surface—properties. Currently available film application technologies require that the process parameters, such as for example concentration, temperature, etc., be thoroughly selected and strictly followed. However, even if all the conditions of film formation are precisely followed, random local variation of the coating regime may occur. This is related to a certain probability of the formation of misorientation zones and microdefects as a result of non-uniform micro- and macrocrystallization processes in the course of solvent removal upon LLC system application onto a substrate surface. In addition, LLC systems based on currently available dyes are characterized by increased probability of non-uniform thickness of the applied coating, which also decreases reproducibility of the film parameters.

The aforementioned disadvantages complicate the formation of films possessing advantageous optical characteristics, make the technology insufficiently reproducible, and require most technological parameters to be thoroughly selected and strictly followed in each stage from application to drying. Accordingly, it is desirable to develop compounds and film application methods that avoid these pitfalls.

SUMMARY OF THE INVENTION

The present invention provides sulfoderivatives of PCTA DBI compounds that do not suffer from the aforementioned difficulties. The provided compounds may be readily and reproducibly applied in thin film structures onto a variety of substrate materials. Solubility may be enhanced through substitution generally along the molecule periphery with certain substituents introduced into desirable positions of the PTCA DBI sulfoderivative molecules. These substituents increase the homogeneity of the crystallization and drying processes, thus increasing the yield of films with reproducible characteristics.

In one embodiment of the present invention, a sulfoderivative compound is provided. The structural formula of the sulfoderivative compound is a sulfonated perylenetetracarboxylic acid dibenzimidazole (PTCA DBI) having a general structural formula selected from one of

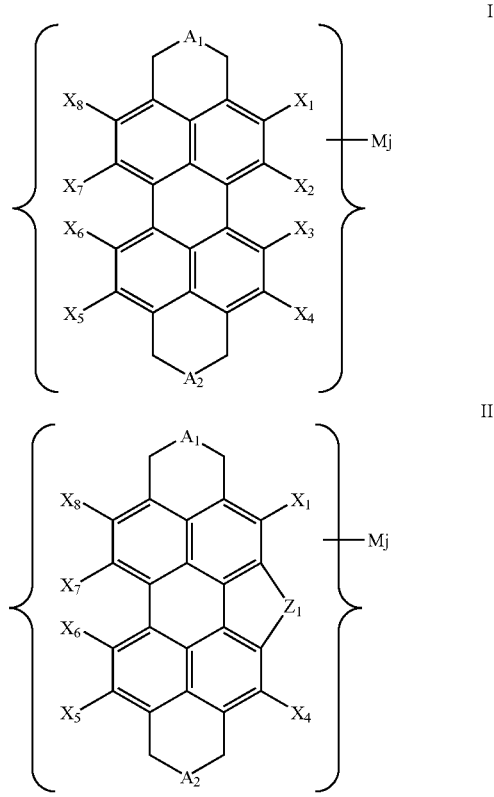

-continued

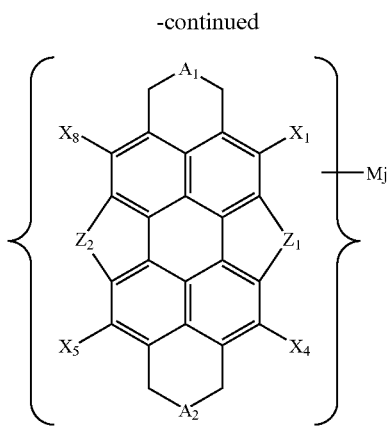

where $X_1$, $X_2$, $X_3$, $X_4$, $X_5$, $X_6$, $X_7$, and $X_8$ are peripheral substituents individually selected from —H, —OH, and —SO$_3$H, such that at least one of the peripheral substituents is not H; M is one or more counter ions and j is the number of counter ions associated with a molecule; $Z_1$ and $Z_2$ are bridging substituents individually selected from —O—, —SO$_2$—, —SO$_2$O—; $A_1$ and $A_2$ are fragments having the general structural formula

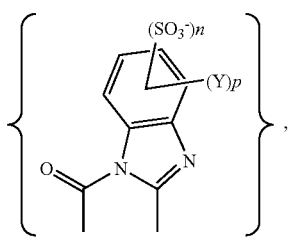

Y is one or more fragments substituents individually selected from —H, —Cl, —F, —Br, -Alk, —OH, —OAlk, —NO$_2$, and —NH2; n is an integer selected from 0, 1, and 2; and p is an integer selected from 0, 1, 2, 3, and 4.

In other, alternative embodiments, the present invention provides lyotropic liquid crystal systems and anisotropic films comprising one or more of these compounds.

BRIEF DESCRIPTION OF THE DRAWINGS

Other objects and advantages of the present invention will become apparent upon reading the detailed description of the invention and the claims, and upon reference to the drawings, in which:

DETAILED DESCRIPTION OF THE INVENTION

Figure 1:
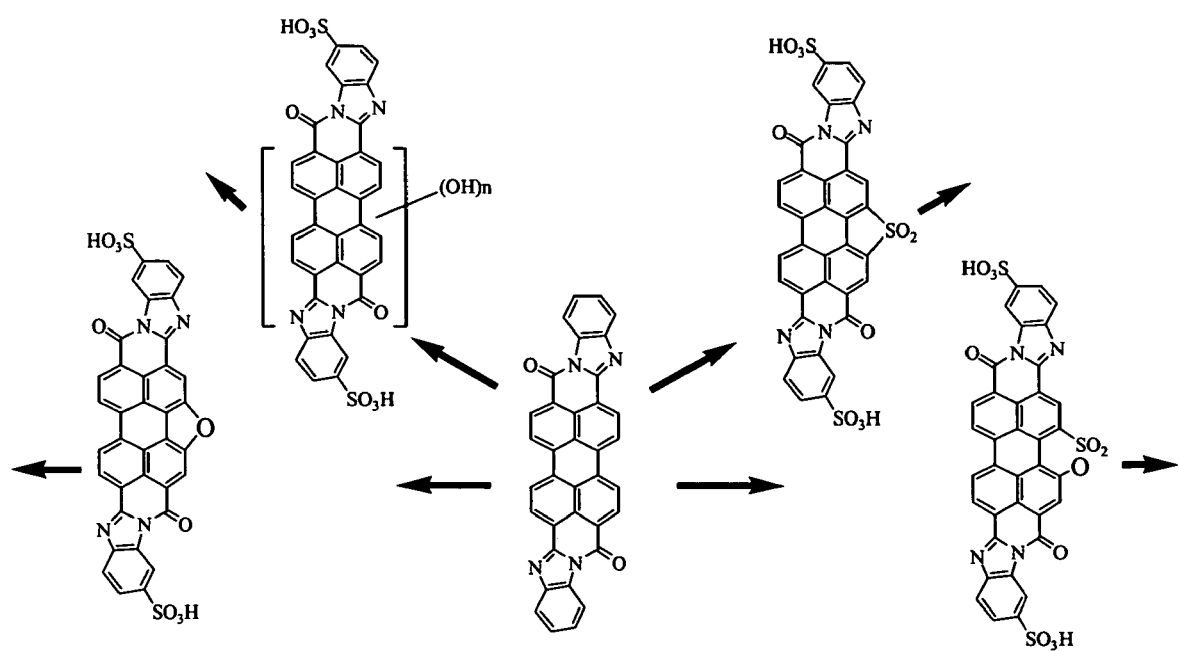
FIG. 1 is a mechanistic diagram illustrating potential sulfonation products of perylenetetracarboxylic acid dibenzimidazole.

The present invention generally provides water-soluble sulfoderivatives of perylenetetracarboxylic acid dibenzimidazole (PTCA DBI) as well as methods for preparing thin anisotropic films and optical elements based on these compounds. The present invention also provides methods of synthesizing sulfonated PTCA DBI derivatives that are capable of forming stable LLC mesophases. Methods for manufacturing anisotropic, at least partially crystalline films based on these compounds are also provided. These films have highly desirable optical properties and working characteristics.

These and other advantages of the present invention may be achieved with sulfoderivatives of perylenetetracarboxylic acid dibenzimidazole (PTCA DBI) having one of the following general structural formulas:

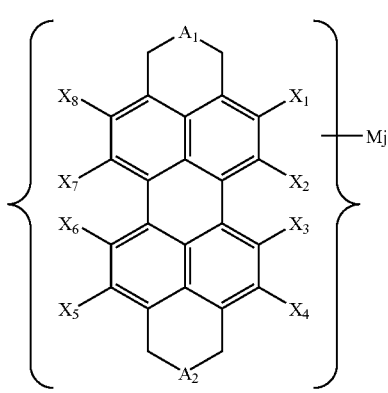

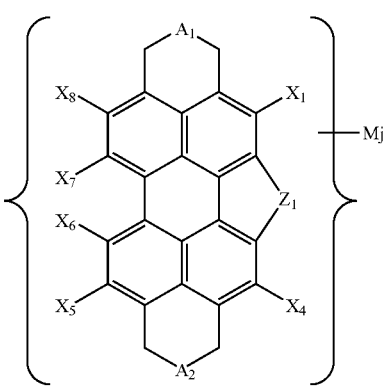

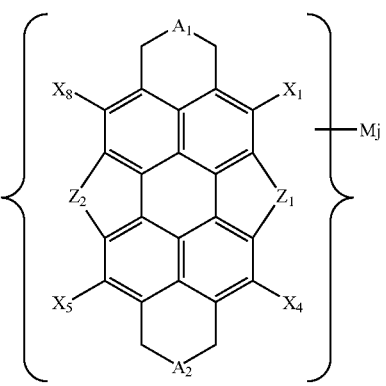

where $X_1$, $X_2$, $X_3$, $X_4$, $X_5$, $X_6$, $X_7$, and $X_8$ are peripheral substituents selected from —H, —OH, and —SO$_3$H, such that at least one of the peripheral substituents is different from H; M is one or more counter ions; and j is the number of counter ions associated with the dye molecule. The number of counter ions, j, may be fractional if the counter ion or counter ions belongs to several molecules. In structures I–III, $A_1$ and $A_2$ are fragments having the general structural formula:

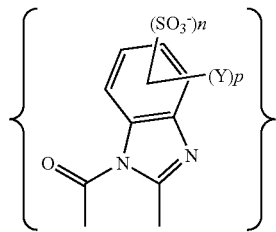

In fragments $A_1$ and $A_2$, Y is a substituent selected from H, Cl, F, Br, Alk, OH, OAlk, $NO_2$, and $NH_2$; p is an integer selected from 0, 1, 2, 3, and 4; and n is an integer selected from 0, 1, and 2. The value of n is advantageously chosen such that such that at least one of fragments $A_1$ or $A_2$ comprises at least one sulfo- group. For values of n greater than, 1, the counter ions M may be different for each of the $SO_3^-$ functional groups. In structures I to III, the one or more counter ions M may include, for example, one or more of cations selected from $H^+$, $NH_4^+$, $K^+$, $Li^+$, $Na^+$, $Cs^+$, $Ca^{++}$, $Sr^{++}$, $Mg^{++}$, $Ba^{++}$, $Co^{++}$, $Mn^{++}$, $Zn^{++}$, $Cu^{++}$, $Pb^{++}$, $Fe^{++}$, $Ni^{++}$, $Al^{+++}$, $Ce^{+++}$, $La^{+++}$, and the like, as well as combinations of such cations.

As shown in general structures II and III, substituents $X_2$ and $X_3$ and/or $X_6$ and $X_7$ in structure I may be replaced with bridging groups $Z_1$ and/or $Z_2$, respectively. In these structures, $Z_1$ and $Z_2$ are individually selected from —O—, —$SO_2$—, and —$SO_2$—O—. In an alternative embodiment of the present invention, substituents $X_2$ and $X_3$ and/or $X_6$ and $X_7$ may interact to form bridges $Z_1$ and/or $Z_2$ that enclose additional heterocyclic systems, such as for example furans, sulfones, and sultones.

The present invention also provides additional new compounds that absorb in the visible spectral range and that are capable of forming stable LLC phases with increased stability. These stable LLC phases may be used in the formation of anisotropic, at least partially crystalline films with highly reproducible, optimal optical characteristics. Films according to the present invention are free of many of the disadvantages of currently available films as described above.

Another embodiment of the present invention provides new organic compounds, the LLC phases of which possess increased stability in a broad range of concentrations, temperatures, and pH values. These compounds simplify the process of film formation, permit the use of widely available commercial equipment for the application of layers, and facilitate production of films with highly reproducible parameters.

Perylenetetracarboxylic acid benzimidazole sulfoderivatives according to the present invention having the general structural formulas I, II, or III may advantageously be cis or trans isomers synthesized by methods available to one of skill in the art. In particular, the PCTA DBI sulfoderivatives of the present invention may be obtained through sulfonation of PTCA DBI under various conditions as shown in FIG. 1. One of skill in the art may readily synthesize these compounds based on an understanding of organic synthesis techniques and the teachings provided herein.

Figure 2:
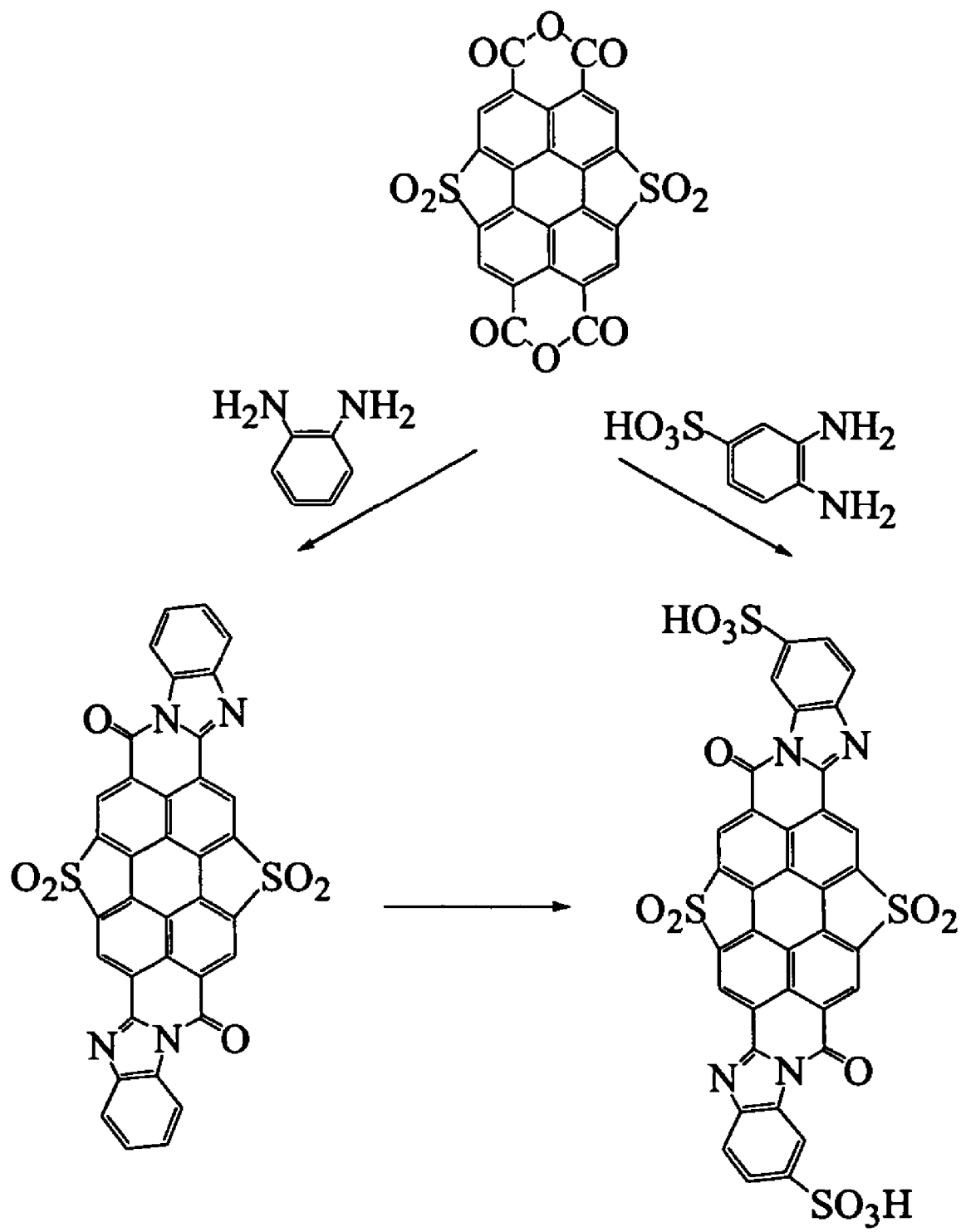
FIG. 2 is a mechanistic diagram illustrating the countersynthesis of disulfones.
Figure 3:
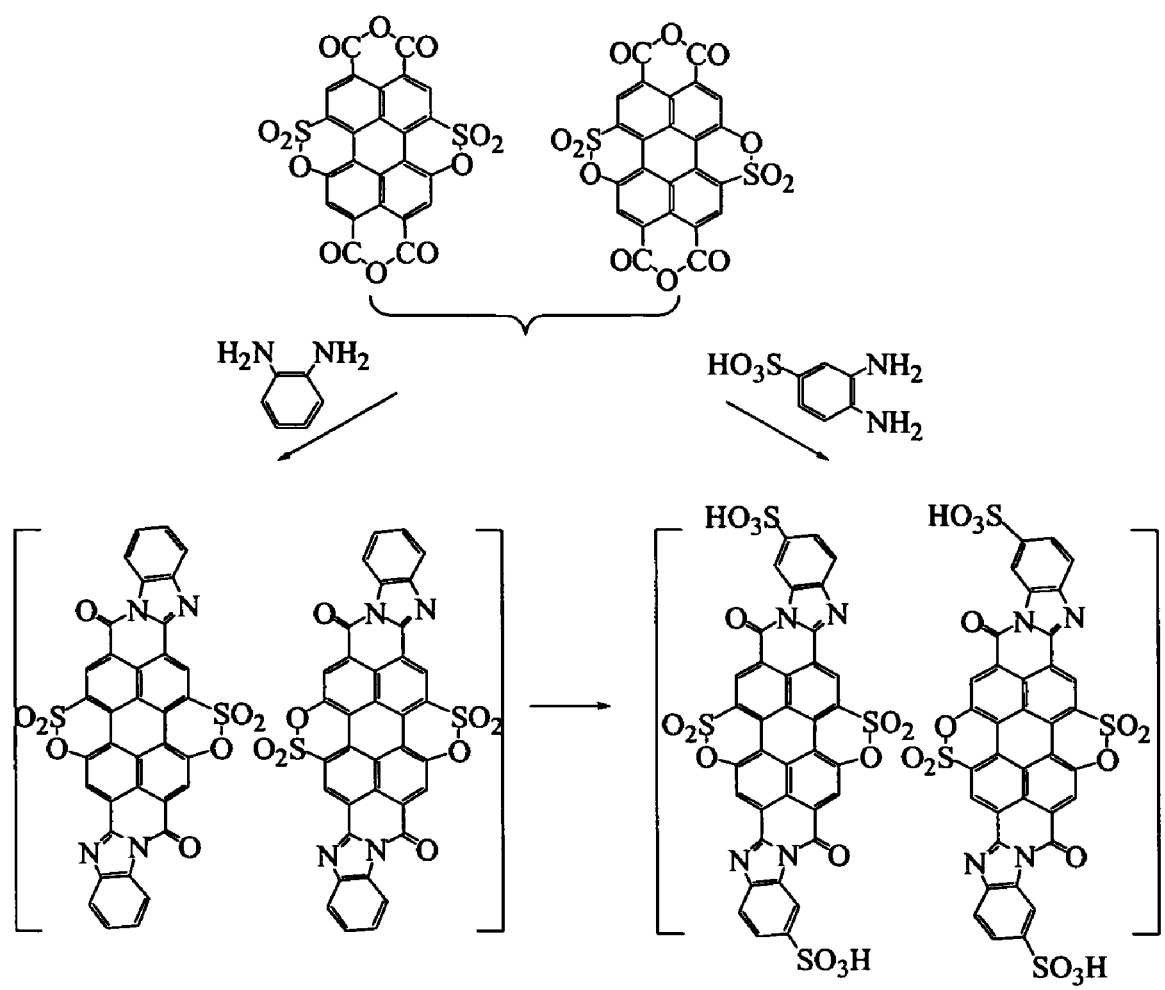
FIG. 3 is a mechanistic diagram illustrating the countersynthesis of disultones.

In addition, sulfoderivatives of the present invention may be obtained from the corresponding PTCA derivatives through condensation with o-phenylenediamime, followed by sulfonation, or through condensation with o-phenylenediamine sulfonate. FIGS. 2 and 3 schematically present the pathways of synthesis of disulfones and disultones of PTCA DBI sulfoderivatives proceeding from PTCA derivatives of known structures.

Alternatively, individual compounds according to the present invention may be obtained through fractionation of mixtures of these compounds. Vice versa mixtures of sulfoderivatives can be obtained through isomerisation of pure compounds.

Perylenetetracarboxylic acid benzimidazole sulfoderivatives with general structural formula I may be readily synthesized under certain preselected conditions. To obtain the target compounds, it is sufficient to determine the initial concentrations of reactants and the technological conditions of synthesis. Most significant parameters are the concentrations of initial reactants, temperature, and reaction duration. These parameters determine the result of synthesis, the product yield, and the ratio of various PTCA DBI sulfoderivatives of formulas I to III) and their isomers' ratio the reaction mass.

Another embodiment of the present invention provides organic compounds whose solutions are characterized by an optimal hydrophilic-hydrophobic balance for LLC system formation. This balance favorably influences the size and shape of supramolecular complexes formed in such systems, as well as the degree of molecular order in these complexes. These properties enhance the desired solubility of compounds according to the present invention and also enhance stability of LLC phases based on these compounds. As a result, reproducibility of the film parameters increases and the film production process may therefore be substantially simplified. The requirements for selection and maintenance of optimal technological conditions at the various production stages become less stringent. In addition, the optical characteristics of the resultant films are improved. The planar molecules of PTCA DBI sulfoderivatives are more homogeneously oriented with respect to the substrate surface, resulting in the dipole moments of electron transitions—generally lying in the planes of the molecules—being better aligned in the direction determined by external orienting factors.

The above tasks can be solved using the disclosed water-soluble compounds, sulfonated PTCA DBI derivatives, which are original compounds not previously described in the literature. Chemical compounds characterized by these structural formulas readily form lyotropic liquid crystal systems and optical anisotropic films with desirable properties.

Sulfonated derivatives of perylenetetracarboxylic acid dibenzimidazole may advantageously include at least one of the more specific structural formulas shown below. These example molecular structures, which are in no way intended to restrict the scope of the present invention, each belong to one of the aforementioned classes of compounds, in particular, to sulfoderivatives of hydroxycompounds, hydroxysulfocompounds, sulfones, sultones, disulfones, disultones, sulfone-sultones, and furan derivatives of PTCA DBI.

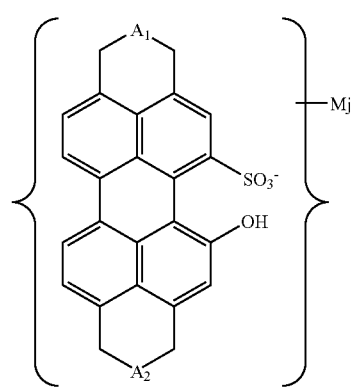
I-a
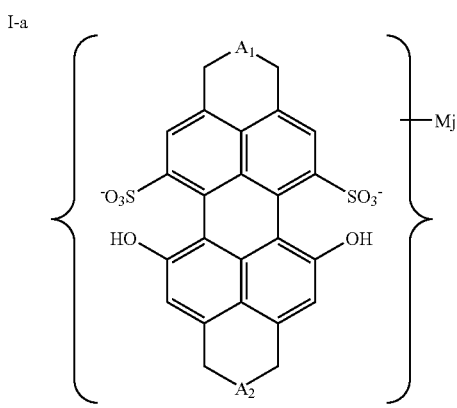
I-b
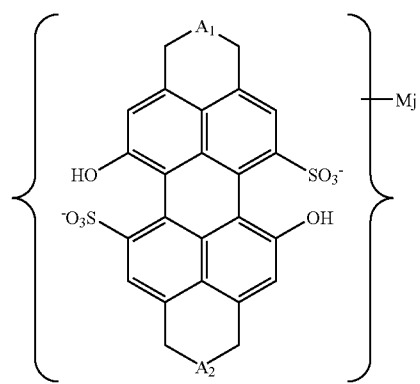
I-c
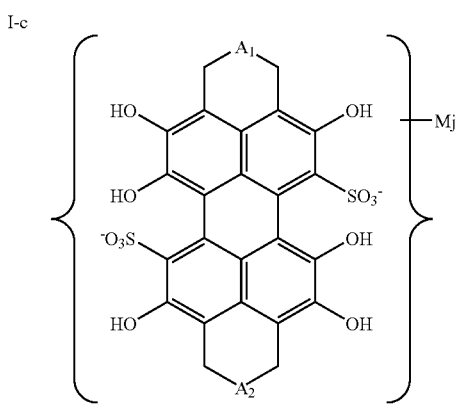
I-d
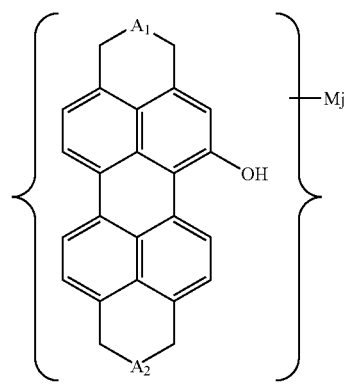
I-e
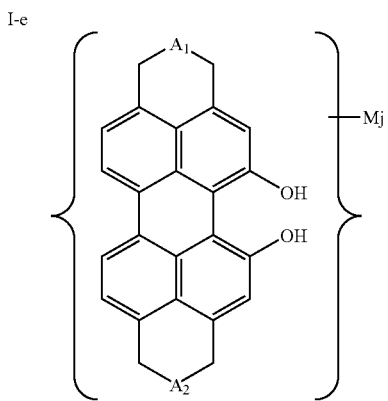
I-f
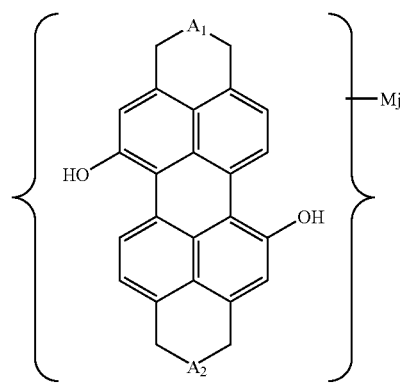
I-g
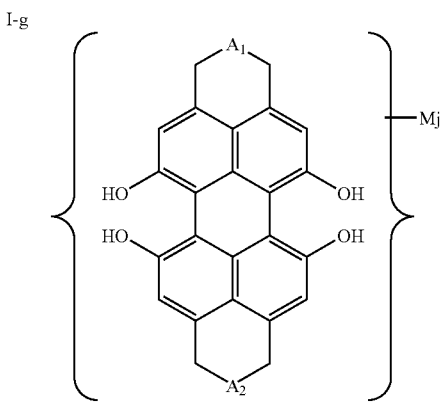
I-h -continued
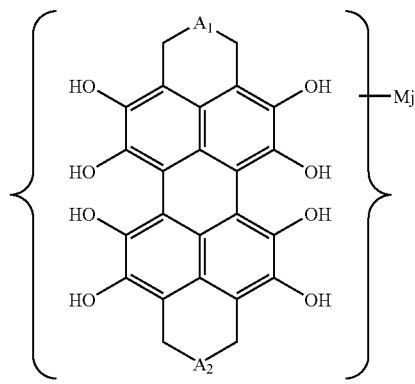
I-I
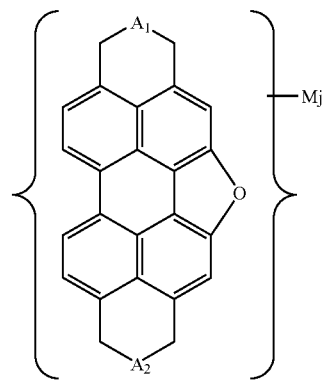
II-a
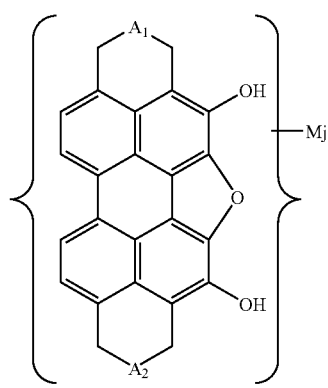
II-b
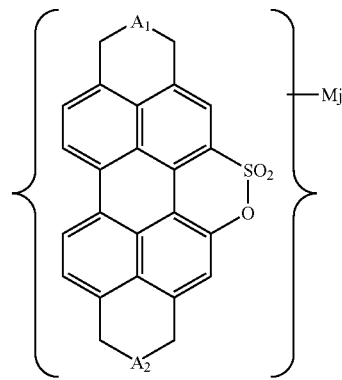
II-c
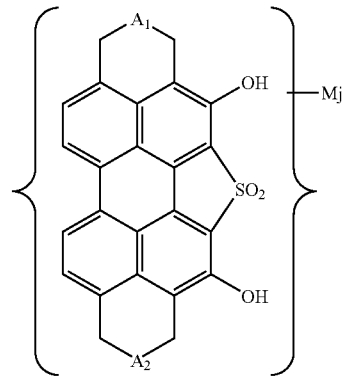
II-d
II-e
II-f
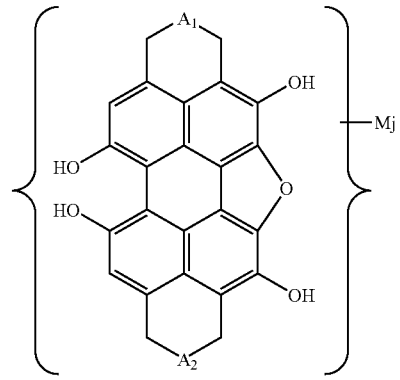
II-g -continued
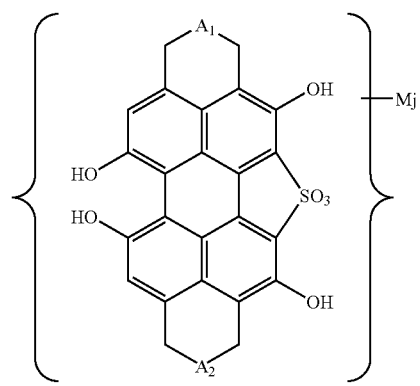 II-h
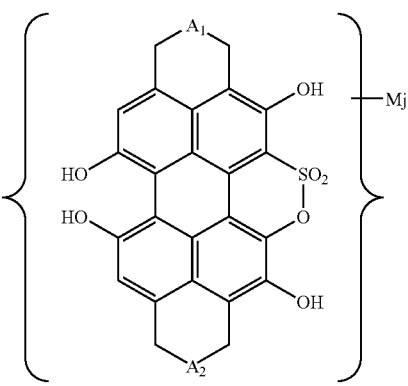 II-i
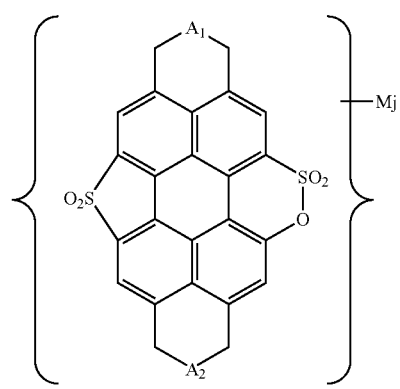 III-a
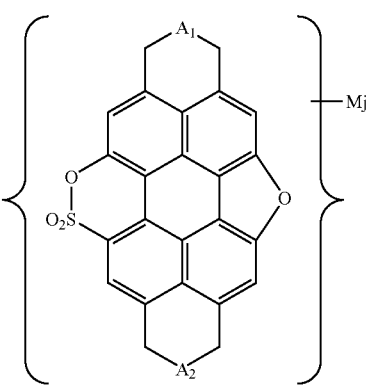 III-b
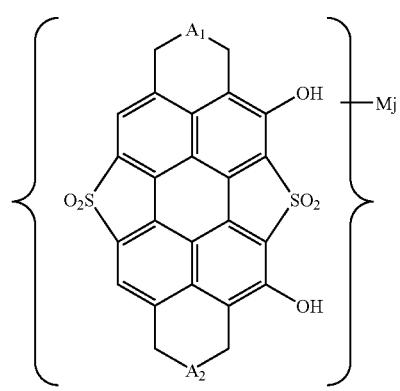 III-c
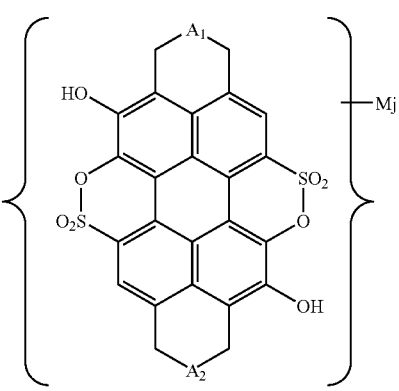 III-d
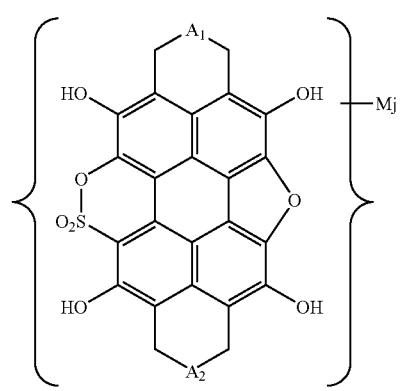 III-e
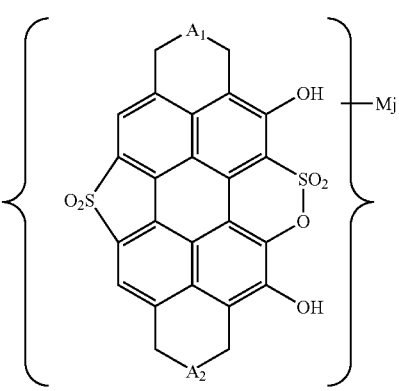 III-f -continued

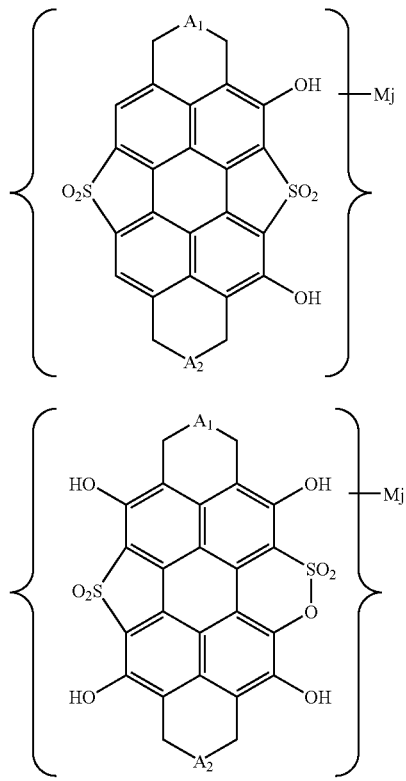

III-g

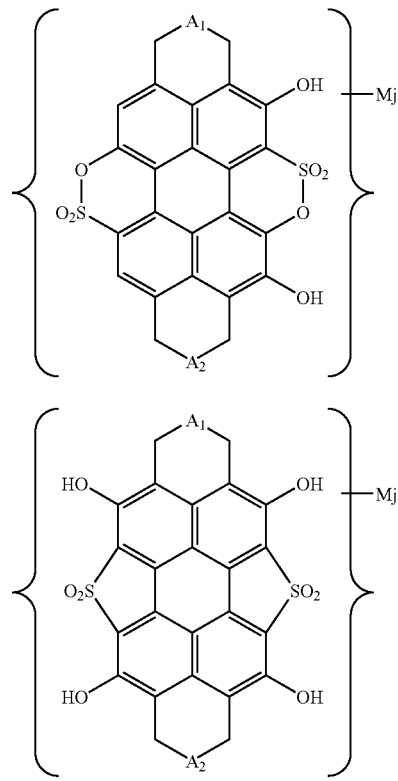

III-h

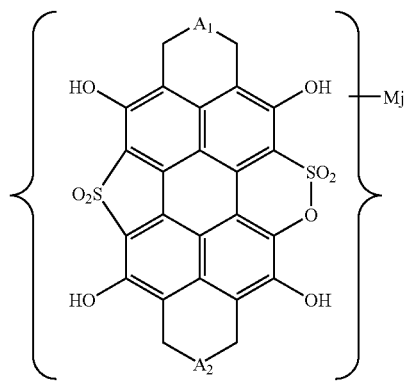

III-i

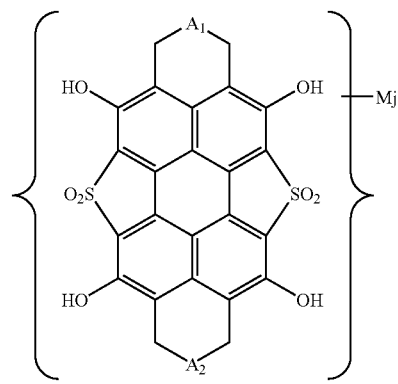

III-j

As in general structural formulas I, II, and III discussed above, M is a counter ion and j is the number of counter ions in the dye molecule. The number of counter ions, j, may be fractional if a counter ion belongs to several molecules. Also as noted above, $A_1$ and $A_2$ are fragments having the general structural formula:

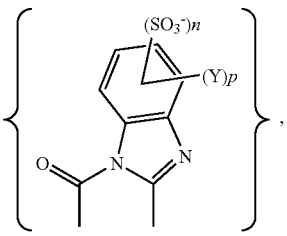

where Y is a substitute selected from —H, —Cl, —F, —Br, —Alk, —OH, —OAlk, —NO$_2$, and —NH$_2$; p is an integer selected from 0, 1, 2, 3 and 4; and n is an integer selected from 0, 1, 2. The value of n is advantageously chosen such that such that at least one of fragments $A_1$ or $A_2$ comprises at least one sulfo- group. For values of n greater than, 1, the counter ions M may be different for each of the $SO_3^-$ functional groups.

In general, compounds having formulas I, II, and III are capable of forming stable LLC phases, both individually and in mixtures with other compounds of this group, with other dichroic dyes capable of forming LLC phases, and with other substances that are generally non-absorbing (colorless) or weakly absorbing in the visible range and capable of forming LLC phases. After removal of the solvent, this LLC phase forms an anisotropic, at least partially crystalline film with reproducibly high optical characteristics. Methods and systems for forming stable LLC phases and resultant anisotropic, at least partially crystalline optical films are described in greater detail in copending U.S. patent application Ser. No. 6,563,640 the disclosure of which is incorporated by reference.

Perylenetetracarboxylic acid dibenzimidazole sulfoderivatives in aqueous solutions typically exhibit maximum optical absorption in the wavelength interval between approximately 550 and 700 nm. The introduction of substituents such as Cl, F, Br, Alk, and —OAlk does not significantly shift the absorption band as compared to the unsubstituted molecules. However, the introduction of amino and hydroxy groups generally leads to broadening of the absorption band and changes the character of the absorption spectrum. By varying the number of sulfonic groups and the number and character of substituents in PTCA DBI derivatives, it is possible to control the hydrophilic-hydrophobic balance of molecular aggregates formed in LLC solutions and to change the solution viscosity.

In another embodiment of the present invention, a method is provided for preparing anisotropic films that may be used as polarizing films. Perylenetetracarboxylic acid benzimidazole sulfoderivatives of the present invention are capable of forming stable lyotropic liquid crystal systems. Liquid crystal solutions (systems) of individual perylenetetracarboxylic acid benzimidazole sulfoderivatives with general structural formulas I, II, or III, as well as mixtures of such compounds, may be prepared by one of skill in the art based on the teachings provided herein.

Liquid crystal solutions (systems) of individual perylenetetracarboxylic acid benzimidazole sulfoderivatives of general structural formulas I, II, and III, as well as mixtures of such compounds, may be applied onto a substrate surface and oriented by any known method such as, for example those described in PCT Publication Nos. WO 94/28073 and WO 00/25155, the disclosures of which are incorporated by reference. The desired orientation can be provided, for example, by applying shear stress or a gravitational, or electromagnetic field. To improve substrate wetting and optimization of the rheological properties of a liquid crystal system, the solution can be modified, for example, by adding plasticizing water-soluble polymers and/or anionic or nonionic surfactants. The system may further comprise one or more water-soluble, low-molecular-weight additives. All additives are advantageously selected so as not to destroy the alignment properties of the liquid crystal system. Subsequent removal of the solvent from the oriented film leads to the formation of an optically anisotropic polycrystalline film with a thickness of 0.2 to 1.2 µm.

Films of the present invention are generally characterized by an approximately 10% increase in reproducibility of the parameters from batch to batch, between different films in the same batch, and over the surface of one film as compared to the films obtained for disulfo PTCA DBI.

Thus, the PTCA DBI sulfoderivatives of the present invention having general structural formulas I, II, or III are capable of forming lyotropic liquid crystal phases and may be used for the obtaining of anisotropic films possessing highly reproducible optical characteristics. These compounds may be also used to obtain isotropic films. A lyotropic liquid crystal system may be applied onto a substrate so as not to be subjected to any external orienting action. This can be achieved through application of the liquid crystal system by methods such as spraying, offset printing, and silk screening. Removal of the solvent leaves the substrate covered with a polycrystalline film with a domain structure that possesses an isotropic optical properties.

Perylenetetracarboxylic acid benzimidazole sulfoderivatives are capable of forming at least partially crystalline films and/or polarizing and/or birefringent films. These perylenetetracarboxylic acid benzimidazole sulfoderivatives may be used in the production of optically isotropic or anisotropic, polarizing and/or phase-retarding and/or birefringent films. The material of an optically isotropic or anisotropic film may comprise at least two compounds selected from the general formulas I, II, and III. Alternatively, the films may comprise at least two specific compounds of at least one of formulas I, II, and III, and comprising at least two different substituents for $X_1$ to $X_8$.

The present invention also encompasses by that the aqueous liquid crystal systems that may be referred to as "water-based ink compositions," and that comprise an individual compound of the disclosed perylenetetracarboxylic acid benzimidazole sulfoderivatives of the general structural formulas I, II, or III or a mixture of at least two such compounds.

Liquid crystal systems according to the present invention are generally based on water or a mixture of water and an organic solvent, that is alternatively miscible with water in any proportion or characterized by limited miscibility with water.

The concentration of a perylenetetracarboxylic acid benzimidazole sulfoderivative or a mixture of perylenetetracarboxylic acid benzimidazole sulfoderivatives in liquid crystal systems of the present invention generally ranges from approximately 3% to 40% by mass. Advantageously, this concentration is in the range of approximately 7% to 20% by mass. The liquid crystal system may further comprise up to 5% by mass of surfactants and/or plasticizers.

The concentration of individual perylenetetracarboxylic acid benzimidazole sulfoderivatives in liquid crystal systems of the present invention may vary, depending on the required properties of the film, as described below. In one embodiment, compounds with general formula I are present with a concentration in the range of approximately 0% to 99% by mass. Alternatively, these compounds are present with a concentration in the range of approximately 0% to 50% by mass. Compounds with general formula II are present with a concentration in the range of approximately 0% to 99% by mass. Alternatively, these compounds are present with a concentration in the range of approximately 0% to 70% by mass. Compounds with general formula III are present with a concentration in the range of approximately 0% to 50% by mass. Alternatively, these compounds are present with a concentration in the range of approximately 0% to 20% by mass. Liquid crystal systems according to the present invention may additionally comprise at least one water-soluble organic dye or a colorless organic compound capable of participating in the formation of a lyotropic liquid crystal phase.

The liquid crystal system may also further comprise at least two compounds with general formula I, II, or III, and/or at least two compounds with at least on one of formulas I, II, and III, comprising at least two different substituents.

Various advantages of the present invention are also provided by obtaining an optically anisotropic film comprising either individual perylenetetracarboxylic dibenzimidazole sulfoderivatives of the general structural formulas I, II, or III or a mixture of such compounds. Optically anisotropic films of the present invention may also further comprise a different organic dye or some colorless compound. These anisotropic films are generally at least partially crystalline.

The optically anisotropic films of the present invention may be obtained by applying a liquid crystal system onto a substrate, followed by orienting action and drying.

EXPERIMENTAL

A number of experiments were conducted according the method and system of the present invention. These experiments are intended for illustration purposes only, and are not intended to limit the scope of the present invention in any way.

Example 1

Synthesis of a mixture of isomeric disulfonic acids of PTCA DBI sulfones from PTCA sulfone was achieved as follows.

Stage 1a. Condensation of PTCADA monosulfone with o-phenylenediamine. 40 ml of acetic acid and 1.5 g of o-phenylenediamine were added to a suspension of 2 g of PTCA dianhydride (PTCADA) monosulfone in 50 ml of 4% NaOH solution. The reaction mixture was heated and kept boiled for 5 hours. The formed precipitate was filtration and washed with ethanol. The process yielded 2.1 g of compounds of the following structural formulas.

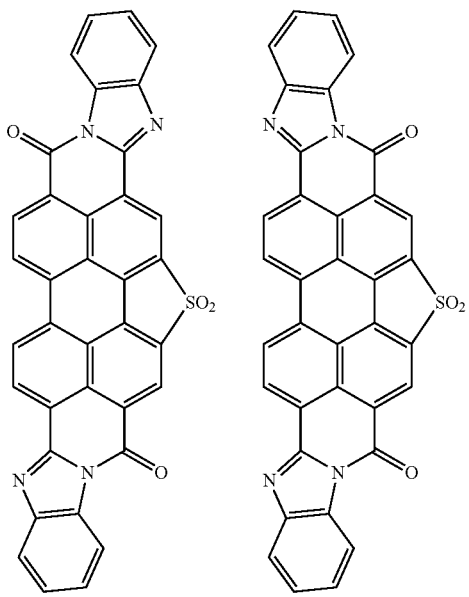

The mass spectrum (VISION 2000) measured molecular ion (negative polarity) was at 598.8 (m/z), and the calculated molecular weight was 598.59.

Stage 1b. Sulfonation of the product of PTCADA monosulfone condensation with o-phenylenediamine. The product of stage 1a (1.5 g) was sulfonated in 6 ml of 4% oleum for 10 hours at 100° C. The reaction mass was then diluted with 10 ml of water. The precipitate was separated by filtration and washed with acetic acid. The process yielded 1.8 g of compounds of the following structural formulas

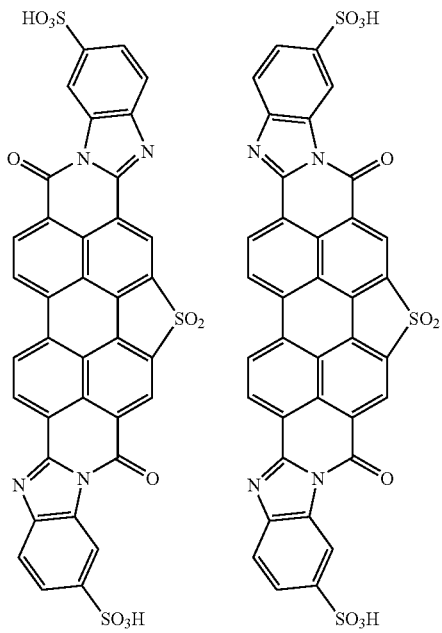

Stage 1c. Condensation of monosulfone of PTCADA with o-phenylenediamine sulfonate. 1.0 g o-phenylenediamine sulfonate was added to a suspension of 1 g PTCADA monosulfone in 30 ml of acetic acid and 10 ml of DMF. The mixture was boiled for 8 hours. The precipitate was separated by filtration and washed with an aqueous ethanol solution. The process yielded 2 g of compounds of the same structural formulas as was obtained at the stage 1b.

The mass spectrum (VISION 2000) measured molecular ion (negative polarity) was at 759.2 (m/z), and the calculated molecular weight was 758.72.

Example 2

Synthesis of disulfonic acid of trans-PTCA DBI sulfone by sulfonation of trans-PTCA DBI was achieved as follows.

Trans-PTCA DBI (5.3 g) was introduced by portions into 25 ml of 35% oleum and sulfonated for 8 hours at 90° C. Then the reaction mass was sequentially diluted, first with 92% aqueous sulfuric acid to monohydrate and then with water to a sulfuric acid concentration of 55%. The precipitate was separated by filtration, triply resuspended in acetic acid, and dried to obtain 7.1 g of a compound of the structural formula

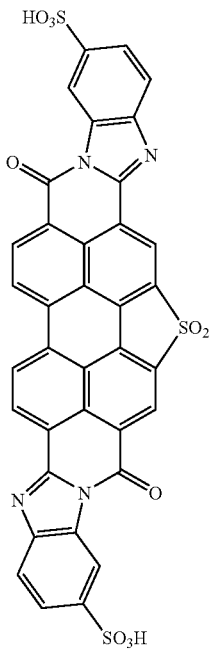

The mass spectrum (VISION 2000) was the following: molecular ion (negative polarity) of 758.4 m/z, and calculated molecular weight of 758. Elemental analysis measured (%) C, 56.72, 56, 80; H, 1.94; 1.66; N, 7.31, 7.39; S, 12.32, 12.40 for $C_{36}H_{14}N_4O_{10}S_3$. Calculated values were (%) C, 56.99; H, 1.86; N, 7.38; O, 21.09; S, 12.68. Infrared spectrum (IR-Fourier spectrometer FSM-1201, film on the windows KRS-5) peaks were located at 1229.4, 1179.7 (sulfonic groups), 1074.0, 1030.5 (sulfonic groups), 1324.7 (sulfone), 1699.6 (carbonyl). The electron spectrum (spectrometer Ocean PC 2000, aqueous solution) of the sample had $\lambda_{max}$=600 nm and 675 nm.

Example 3

Synthesis of a mixture of isomeric disulfonic acids of PTCA DBI sultones from PTCA sultones was achieved as follows.

Stage 3a. Condensation of PTCADA monosultone with o-phenylenediamine. 1.5 g of o-phenylenediamine was added to a suspension of 2 g of PTCADA monosultone in a mixture of 20 ml of acetic acid and 20 ml of DMF. The reaction mass was heated for 2 hours. The formed precipitate was separated by filtration and washed with ethanol. The process yielded 2.4 g of compounds of the following structural formulas

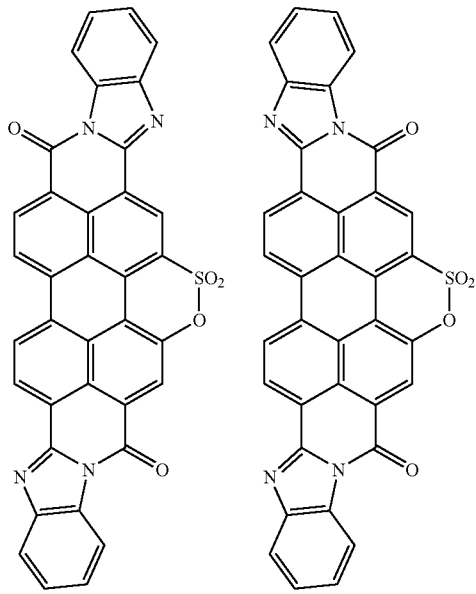

Stage 3b. Sulfonation of the product of PTCADA monosultone condensation with o-phenylenediamine. The product of stage 1a (1 g) was sulfonated in 5 ml of 4% oleum for 8 hours at 100 C. The reaction mass was then diluted with 10 ml of water. The precipitate was separated by filtration and washed with acetic acid. The process yielded 1.1 g of compounds of the following structural formulas

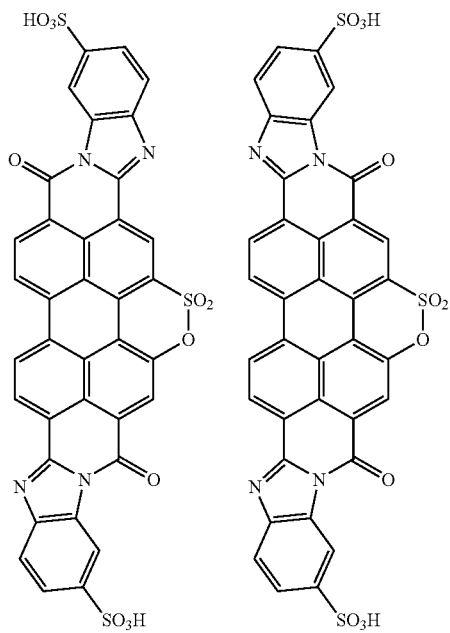

Stage 3c. Condensation of monosultone of PTCADA with o-phenylenediamine sulfonate. 1.5 g of o-phenylenediamine sulfonate was added to a suspension of PTCADA monosultone (1 g) in 30 ml of acetic acid. The mixture was boiled for 8 hours. The formed precipitate was separated by filtration and washed with an aqueous ethanol solution. The process yielded 1.8 g of compounds of the same structural formulas as was obtained at the stage 3b.

The mass spectrum (VISION 2000) measured molecular ion negative polarity was at 773.1 (m/z), and the calculated molecular weight was 774.7. The electron absorption spectrum (spectrometer Ocean PC2000, aqueous solution) of the sample had $\lambda_{max}$=590 nm.

Example 4

Synthesis of disulfonic acid of cis-PTCA DBI sultone by sulfonation of PTCA DBI was achieved as follows.

Cis-PTCA DBI (5.3 g) was introduced by portions into 25 ml of 10% oleum and sulfonated for 8 hours at 190 to 200° C. Then the reaction mass was sequentially diluted, first with 92% aqueous sulfuric acid to monohydrate and then with water to a sulfuric acid concentration of 60%. The formed precipitate was separated by filtration, triply resuspended in acetic acid, and dried to obtain 6.8 g of a compound of the following structural formula

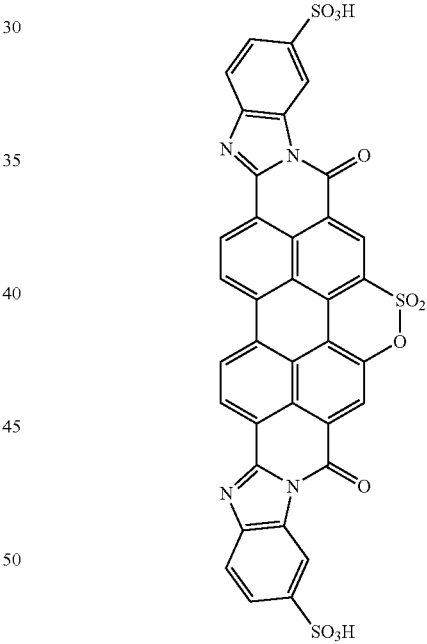

The mass spectrum (VISION 2000) measured molecular ion negative polarity was at 772.4(m/z), with a calculated molecular weight of 774.1. Elemental analysis measured (%) C, 55.51, 55.58; H, 1.64, 1.71; N, 7.00, 7.11; S, 12.65, 12.58 for $C_{36}H_{14}N_4O_{11}S_3$. Calculated values were (%) C 55.81; H, 1.82; N, 7.23; O, 22.72; S, 12.42. Infrared spectrum (IR-Fourier spectrometer FSM-1201, film on the windows KRS-5) peaks were located at 1237.7, 1179.7 (sulfonic groups), 1074.0, 1030.5 (sulfonic groups), 1431.4 (sultone), 1712.3 (carbonyl). The electron spectrum (spectrometer Ocean PC2000, aqueous solution) of the sample had $\lambda_{max}$=580 nm and 660 nm.

Example 5

Synthesis of a mixture of disulfonic acids of PTCA DBI disultones from PTCA disultones was achieved as follows.

Stage 5a. Condensation of PTCADA disultone with o-phenylenediamine. A suspension of 1 g of PTCADA disultone and 1 g of o-phenylenediamine in 30 ml of acetic acid was boiled for 5 hours. The formed precipitate was separated by filtration and washed with ethanol. The process yielded 1.1 g of compounds of the following structural formulas

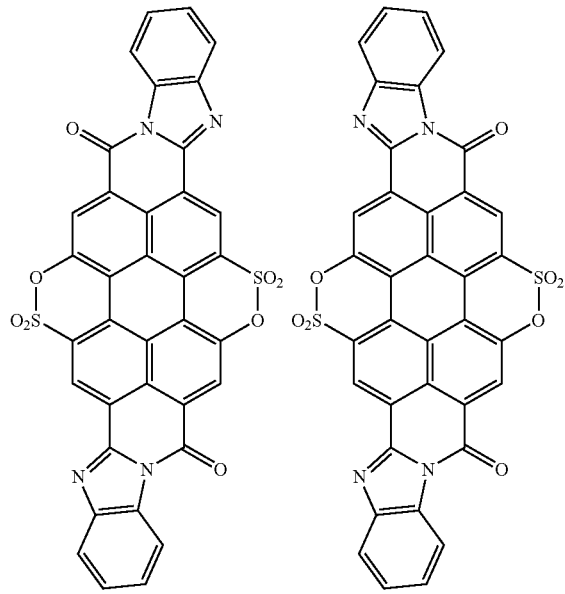

Stage 5b. Sulfonation of the product of PTCADA disultone condensation with o-phenylenediamine. The product of stage 1a (1 g) was sulfonated in 5 ml of 4% oleum for 6 hours at 100 C. The reaction mass was then diluted with 10 ml of water. The precipitate was separated by filtration and washed with acetic acid. The process yielded 1.1 g of compounds of the following structural formulas

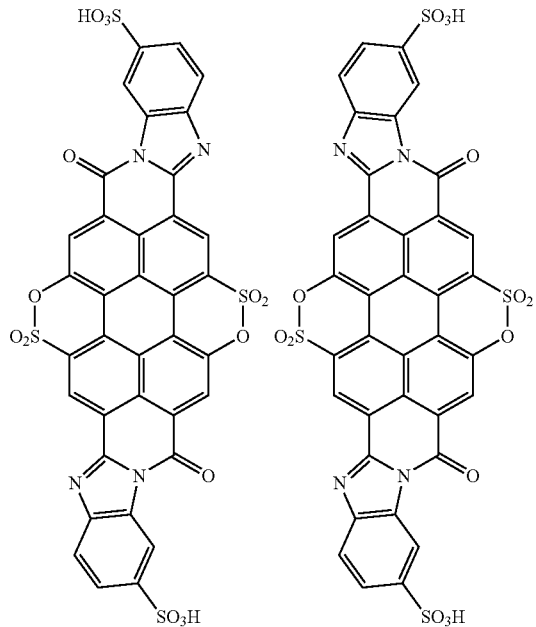

Stage 5c. Condensation of disultone of PTCADA with o-phenylenediamine sulfonate. 1 g of o-phenylenediamine sulfonate was added to a suspension of PTCADA disultone (0.5 g) in acetic acid. The mixture was boiled for 4 hours. The formed precipitate was separated by filtration and washed with an aqueous ethanol solution. The process yielded 0.6 g of compounds of the same structural formulas as was obtained at stage 5b.

The mass spectrum (VISION 2000) measured molecular ion (negative polarity was at 851.4(m/z), with a calculated molecular weight of 852.76. Elemental analysis measured (%) C, 50.72, 50.63; H, 1.28, 1.33; N, 6.47, 6.01; S, 14.74, 14.81 for $C_{36}H_{12}N_4O_{14}S_4$. Calculated values were (%) C, 50.70; H, 1.42; N, 6.57; O, 26.27; S, 15.04. Infrared spectrum (IR-Fourier spectrometer FSM-1201, film on the windows KRS-5) peaks were located at 1237.7, 1179.7 (sulfonic groups), 1074.0, 1030.5 (sulfonic groups), 1431.4 (sultone), 1712.3 (carbonyl).). The electron spectrum (spectrometer Ocean PC2000, aqueous solution) of the sample had $\lambda_{max}$ 580 nm and 660 nm.

Example 6

Synthesis of a mixture of isomeric hydroxysulfonic acids of PTCA DBI from hydroxyl-PTCA was achieved as follows.

Stage 6a. Condensation of monohydroxy-PTCADA with o-phenylenediamine. A suspension of 1 g of monohydroxy-PTCADA and 1.6 g of o-phenylenediamine in 30 ml of acetic acid was boiled for 8 hours. The formed precipitate was separated by filtration and washed with ethanol. The process yielded 1.3 g of compounds of the following structural formulas

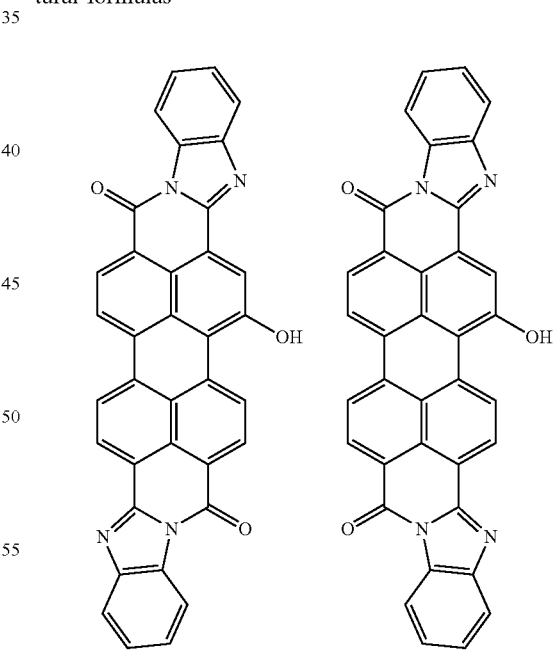

Stage 6b. Sulfonation of the product of monohydroxy-PTCADA condensation with o-phenylenediamine. The product of stage 1a (1 g) was sulfonated in 5 ml of 4% oleum for 12 hours at 100 C. The reaction mass was then diluted with 20 ml of water. The precipitate was separated by filtration and washed with acetic acid. The process yielded 1.2 g of compounds of the following structural formulas

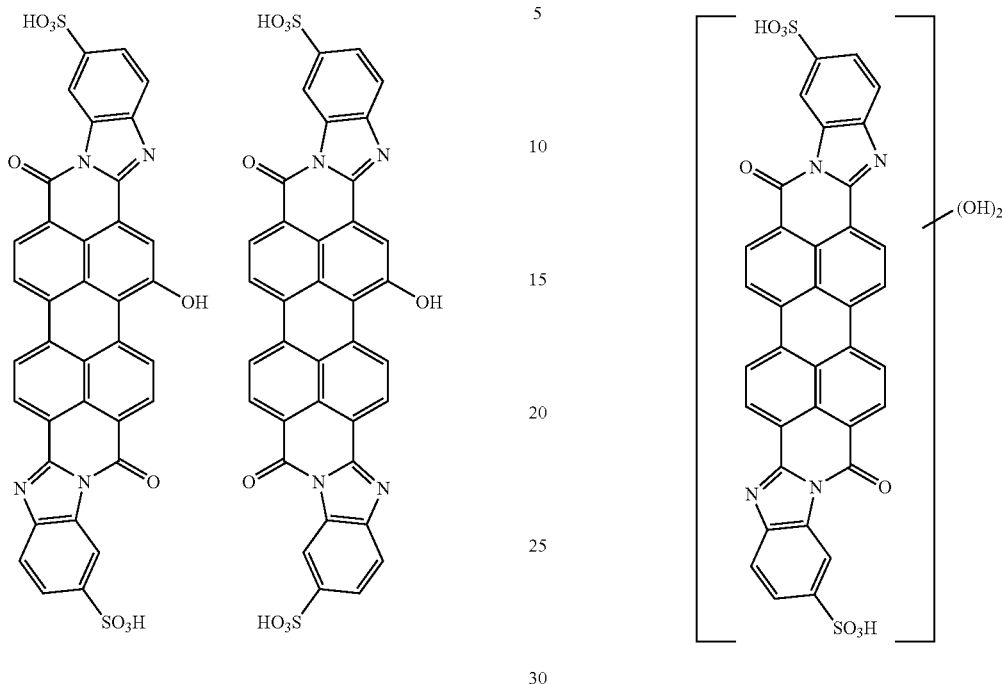

Stage 6c. Condensation of monohydroxy-PTCADA with o-phenylenediamine sulfonate. A mixture of monohydroxy-PTCADA (1 g) and 1.5 g of o-phenylenediamine sulfonate in 30 ml of acetic acid was boiled for 8 hours. The precipitate was separated by filtration and washed with an aqueous ethanol solution. The process yielded 1.2 g of compounds of the same structural formulas as was obtained at the stage 6d.

The mass spectrum (VISION 2000) was the following: molecular ion negative polarity of 711.5. (m/z), with a calculated molecular weight of 712.67.

Example 7

Synthesis of dihydroxysulfonic acid of trans-PTCA DBI by sulfonation of PTCA DBI was achieved as follows.

Trans-PTCA DBI (5.3 g) was introduced by portions into 20 ml of 10% oleum and stirred for 8 hours, after which the oleum concentration was increased to 30% and sulfonation was continued for 10 hours at 120° C. Then the reaction mass was sequentially diluted, first with 92% aqueous sulfuric acid to monohydrate and then with water to a sulfuric acid concentration of 75%. The formed precipitate was separated by filtration, triply resuspended in acetic acid, and dried to obtain 6.0 g of a compound of the following structural formula The mass spectrum (VISION 2000) measured molecular ion negative polarity was at 727.9 (m/z), with a calculated molecular weight of 728.67. Elemental analysis measured (%) C, 59.17, 60.12; H, 2.27, 2.30; N, 7.20, 7.35; S, 9.12, 9.24 for $C_{36}H_{16}N_4O_{10}S_2$. Calculated values were (%) C, 59.34; H, 2.21; N, 7.69; O, 21.96; S, 8.80. Infrared spectrum (IR-Fourier spectrometer FSM-1201, film on the windows KRS-5) peaks were located at 1237.7, 1179.7 (sulfonic groups), 1074.0, 1030.5 (sulfonic groups), 896 (hydroxyl), 1710.0 (carbonyl). The electron spectrum (spectrometer Ocean PC2000, aqueous solution) of the sample had λmax=720 nm.

Example 8

Synthesis of a mixture of isomeric dihydroxydisulfonic acids of PTCA DBI from dihydroxy-PTCA was achieved as follows.

Stage 8a. Condensation of dihydroxy-PTCADA with o-phenylenediamine. A suspension of 1.5 g of dihydroxy-PTCADA and 3 g of o-phenylenediamine in 30 ml of acetic acid was boiled for 8 hours. The formed precipitate was separated by filtration and washed with ethanol. The process yielded 1.8 g of compounds of the following structural formulas

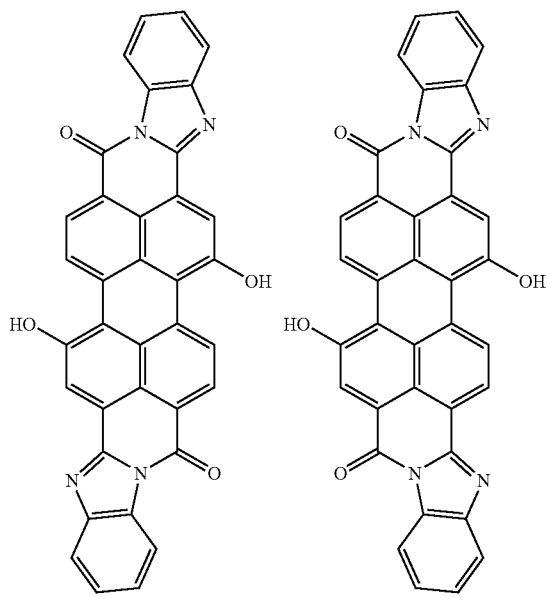

Stage 8b. Sulfonation of the product of dihydroxy-PTCADA condensation with o-phenylenediamine. The product of stage 1a (1 g) was sulfonated in 5 ml of 4% oleum for 12 hours at 100 C. The reaction mass was then diluted with 20 ml of water. The precipitate was separated by filtration and washed with acetic acid. The process yielded 1 g of compounds of the following structural formulas

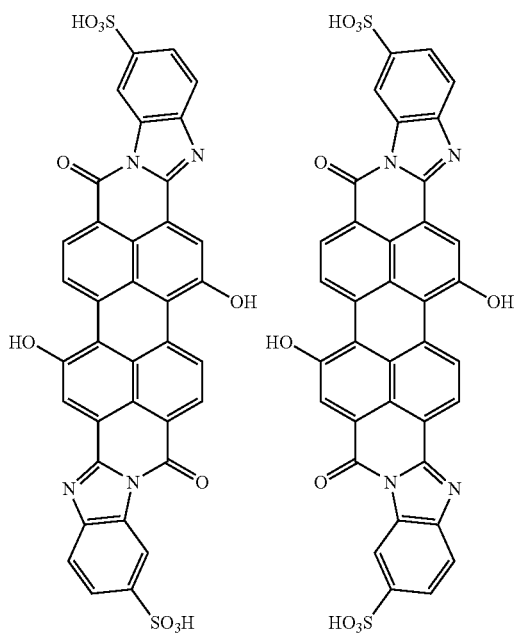

Stage 8c. Condensation of dihydroxy-PTCADA with o-phenylenediamine sulfonate. A mixture of dihydroxy-PTCADA (1 g) and 1.5 g of o-phenylenediamine sulfonate in 40 ml of acetic acid was boiled for 8 hours. The precipitate was separated by filtration and washed with an aqueous ethanol solution. The process yielded 1.1 g of compounds with the same structural formulas as was obtained at the stage 8b.

The mass spectrum (VISION 2000) was the following: molecular ion negative polarity of 727.5. (m/z), with a calculated molecular weight of 728.67.

Example 9

Synthesis of disulfonic acid of cis-PTCA DBI furane by sulfonation of PTCA DBI was achieved as follows.

Cis-PTCA DBI (5.0 g) was introduced by portions into 25 ml of 45% oleum and sulfonated for 5 hours at 60° C. Then the reaction mass was sequentially diluted, first with 92% aqueous sulfuric acid to monohydrate and then with water to a sulfuric acid concentration of 65%. The formed precipitate was separated by filtration, triply resuspended in acetic acid, and dried to obtain 6.5 g of a compound of the following structural formula

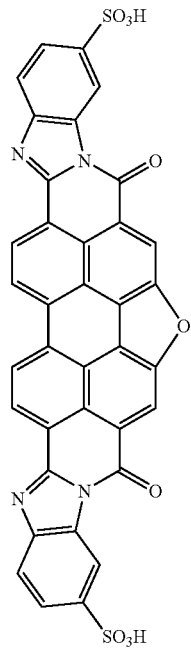

The mass spectrum (VISION 2000) was the following: molecular ion negative polarity of 709.4 (m/z), with a calculated molecular weight of 710.65. Elemental analysis measured (%) C, 60.66, 60.10; H, 2.09, 2.27; N, 7.39, 7.32; S, 9.51, 9.41 for $C_{36}H_{14}N_4O_9S_2$. Calculated values were (%) C, 60.84; H, 1.99; N, 7.88; O, 20.26; S, 9.02. The electron spectrum (spectrometer Ocean PC2000, aqueous solution) of the sample had $\lambda_{max}$=600 nm.

Other derivatives corresponding to general structures I, II, and III may be synthesized by analogous procedures, for example through sulfonation of PTCA DBI isomers or mixtures, by condensation of the corresponding PTCA derivatives with followed by sulfonation, by condensation of these PTCA derivatives with o-phenylenediamine sulfonate, or by equivalent methods.

Example 10

A liquid crystal composition and film comprising PTCA DBI dihydroxydisulfonic acid was prepared as followed and the film's optical characteristics were determined.

A solution of 10 g of a PTCA DBI dihydroxydisulfonic acid (Example 7) in 79.9 ml of deionized water was prepared by stirring at 20° C. and neutralized by ammonia to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by transmission spectra measured on a Cary-500 spectrophotometer in a wavelength range from 190 to 800 nm using a light beam polarized along the direction of film application ($T_{par}$) and in the perpendicular direction ($T_{per}$) relative to the solution application direction. At a wavelength of $\lambda=650$ nm corresponding to maximum absorption, the dichroic ratio $K_d=\log(T_{par})/\log(T_{per})$ was equal to 35; at a film transmission of 35%, the contrast ratio was C/R=200.

Example 11

A liquid crystal composition and film comprising a mixture of PTCA DBI sulfoderivatives was prepared as follows and the film's optical characteristics were determined.

A solution of 10 g of a mixture of PTCA DBI sulfoderivatives, including 20% of sulfone (Example 2), 25% of sultone (Example 4), and 55% of hydroxysulfonic acid (Example 6b) in 79.9 ml of deionized water was prepared by stirring at 20° C. and neutralized by ammonia. A solution of 0.1 g of sulfonol in 10 ml of water was added to this solution. The mixture was thoroughly stirred to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by transmission spectra measured on a Cary-500 spectrophotometer in a wavelength range from 190 to 800 nm using a light beam polarized along the direction of film application ($T_{par}$) and in the perpendicular direction ($T_{per}$) relative to the solution application direction. At a wavelength of $\lambda=650$ nm corresponding to maximum absorption, the dichroic ratio $K_d=\log(T_{par})/\log(T_{per})$ was equal to 32; at a film transmission of 35%, the contrast ratio was C/R=200.

Example 12

A liquid crystal composition and film of a mixture of PTCA DBI disulfoderivatives with indanthrone derivatives was prepared the film's optical characteristics were determined.

A solution of 10 g of a mixture of PTCA DBI sulfone disulfonic acid (Example 2, 40% by mass) and indanthrone trisulfonic acid (60% by mass) in 79.9 ml of deionized water was prepared by stirring at 20° C. and neutralized by ammonia. A solution of 0.1 g of sulfonol in 10 ml of water was added to this solution. The mixture was thoroughly stirred to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by transmission spectra measured on a Cary-500 spectrophotometer in a wavelength range from 190 to 800 nm using a light beam polarized along the direction of film application ($T_{par}$) and in the perpendicular direction ($T_{per}$) relative to the solution application direction. At a wavelength of $\lambda=650$ nm corresponding to maximum absorption, the dichroic ratio $K_d=\log(T_{par})/\log(T_{per})$ was equal to 30; at a film transmission of 35%, the contrast ratio was $K_d=250$.

Example 13

A liquid crystal composition and film comprising a mixture of PTCA DBI disulfoderivatives with derivatives of indanthrone and naphthalenetetracarboxylic acid was prepared and the film's optical characteristics were determined.

A solution of 10 g of a mixture including PTCA DBI sulfone disulfonic acid (Example 2, 10% by mass), PTCA DBI dihydroxydisulfonic acid (Example 8b, 30% by mass), PTCA DBI monohydroxydisulfonic acid (Example 6b, 10% by mass), indanthrone trisulfonic acid (40% by mass), and NTCA DBI disulfonic acid (10% by mass), (in 79.9 ml of deionized water was prepared by stirring at 20° C. and neutralized by ammonia. A solution of 0.1 g of sulfonol in 10 ml of water was added to this solution. The mixture was thoroughly stirred to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by transmission spectra measured on a Cary-500 spectrophotometer in a wavelength range from 190 to 800 nm using a light beam polarized along the direction of film application ($T_{par}$) and in the perpendicular direction ($T_{per}$) relative to the solution application direction. At a wavelength of $\lambda=650$ nm corresponding to maximum absorption, the dichroic ratio $K_d=\log(T_{par})/\log(T_{per})$ was equal to 34; at a film transmission of 35%, the contrast ratio was C/R=300.

In addition to those compounds explicitly described above, all compounds characterized by general formulas I, II, and III provide stable lyotropic liquid crystal systems which can be used for obtaining optically anisotropic films with high performance characteristics and high reproducibility.

The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents

What is claimed is:

1. A sulfoderivative compound, comprising:
a sulfonated perylenetetracarboxylic acid dibenzimidazole (PTCA DBI) having a general structural formula selected from one of

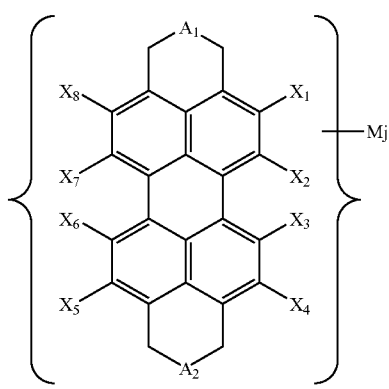

I

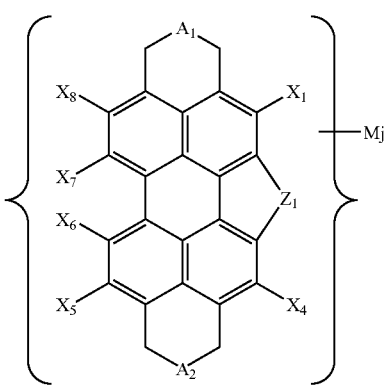

II

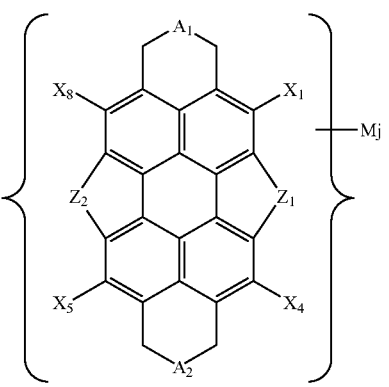

III where $X_1$, $X_2$, $X_3$, $X_4$, $X_5$, $X_6$, $X_7$, and $X_8$ are peripheral substituents individually selected from —H, —OH, and —SO$_3$H, such that at least one of the peripheral substituents is not H, and at least one of $X_1$ to $X_8$ in formula I is OH;

M is one or more counter ions and j is the number of counter ions associated with a molecule;

$Z_1$ and $Z_2$ are bridging substituents individually selected from —O—, —SO$_2$—, —SO$_2$—O—; $A_1$ and $A_2$ are fragments having the general structural formula

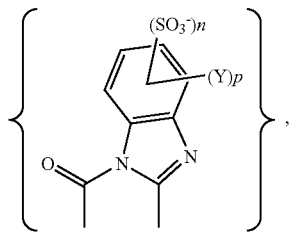

Y is one or more fragments substituents individually selected from —H, —Cl, —F, —Br, —Alk, —OH, —OAlk, —NO$_2$, and —NH$_2$;

n is an integer selected from 0, 1, and 2; and p is an integer selected from 0, 1, 2, 3, and 4.

2. The sulfoderivative of claim 1, wherein fragments $A_1$ or $A_2$ together comprise at least one SO$_3^-$ group.

3. The sulfoderivative of claim 1, wherein the counter ion or counter ions are shared by more than one sulfoderivative molecule.

4. The sulfoderivative of claim 1, wherein the counter ion or counter ions, M, are individually selected from H$^+$, NH$_4^+$, K$^+$, Li$^+$, Na$^+$, Cs$^+$, Ca$^{++}$, Sr$^{++}$, Mg$^{++}$, Ba$^{++}$, Co$^{++}$, Mn$^{++}$, Zn$^{++}$, Cu$^{++}$, Pb$^{++}$, Fe$^{++}$, Ni$^{++}$, Al$^{+++}$, Ce$^{+++}$, and La$^{+++}$.

5. The sulfoderivative of claim 1, wherein the sulfoderivative is capable of forming a stable lyotropic liquid crystal system.

6. The sulfoderivative of claim 1, wherein the sulfoderivative is capable of forming an optically isotropic or anisotropic film.

7. A sulfoderivative compound, comprising:
a sulfonated perylenetetracarboxylic acid dibenzimidazole (PTCA DBI) having a general structural formula selected from one of

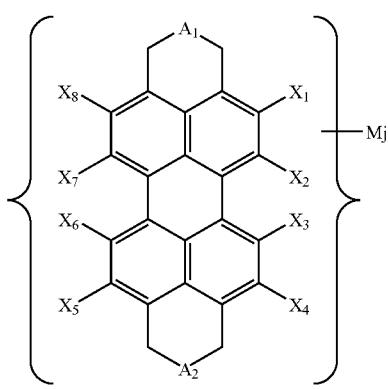

I

-continued

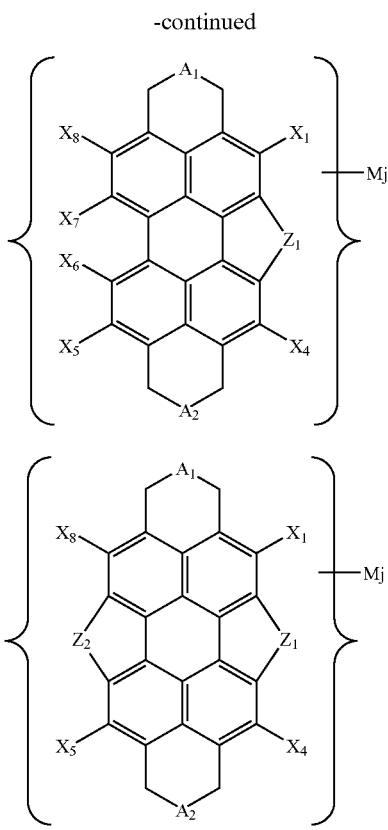

where $X_1$, $X_2$, $X_3$, $X_4$, $X_5$, $X_6$, $X_7$, and $X_8$ are peripheral substituents individually selected from —H, —OH, and —SO$_3$H, such that at least one of the peripheral substituents is not H;

M is one or more counter ions and j is the number of counter ions associated with a molecule;

$Z_1$ and $Z_2$ are bridging substituents individually selected from —O—, —SO$_2$—, —SO$_2$—O—;

$A_1$ and $A_2$ are fragments having the general structural formula

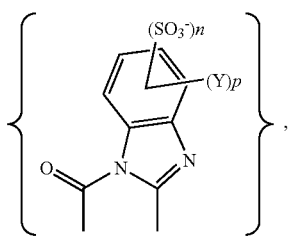

Y is one or more fragments substituents individually selected from —H, —Cl, —F, —Br, —Alk, —OH, —OAlk, —NO$_2$, and —NH$_2$;

n is an integer selected from 0, 1, and 2; and p is an integer selected from 0, 1, 2, 3, and 4, wherein the sulfoderivative is capable of forming an at least partially crystalline film.

8. A lyotropic liquid crystal (LLC) system comprising at least one sulfoderivative of claim 1.

9. The LLC system of claim 8, wherein the LLC system is based on water.

10. The LLC system of claim 8, wherein the LLC system is based on a mixture of water and an organic solvent miscible with water.

11. The LLC system of claim 8, wherein the concentration of PTCA DBI sulfoderivatives in the LLC system is in the range of approximately 3% to 40% by mass.

12. The LLC system of claim 8, further comprising up to 5% by mass of surfactants.

13. The LLC system of claim 8, further comprising up to 5% by mass of plasticizers.

14. The LLC system of claim 8, further comprising:
a sulfoderivative of structural formula I in a concentration range of approximately 0% to 99% by mass;
a sulfoderivative of structural formula II in a concentration range of approximately 0% to 99% by mass; and
a sulfoderivative of structural formula III in a concentration range of approximately 0% to 50% by mass,
wherein the total amount of formulas I to III is 100% by mass.

15. The LLC system of claim 8, further comprising:
a sulfoderivative of structural formula I in a concentration range of approximately 0% to 50% by mass;
a sulfoderivative of structural formula II in a concentration range of approximately 0% to 70% by mass; and
a sulfoderivative of structural formula III in a concentration range of approximately 0% to 20% by mass,
wherein the total amount of formulas I to III is 100% by mass.

16. The LLC system of claim 8, further comprising at least one water-soluble organic dye or an organic compound, the organic dye or organic compound being capable of participating in the formation of the LLC system having at least one sulfoderivative of structural formulas I, II, and III.

17. An optically anisotropic film comprising at least one sulfoderivative of claim 1.

18. The optically anisotropic film of claim 17, wherein the film is formed by depositing a lyotropic liquid crystal system comprising at least one sulfoderivative derivative compound.

19. An optically anisotropic film comprising at least one sulfoderivative which comprises:
a sulfonated perylenetetracarboxylic acid dibenzimidazole (PTCA DBI) having a general structural formula selected from one of

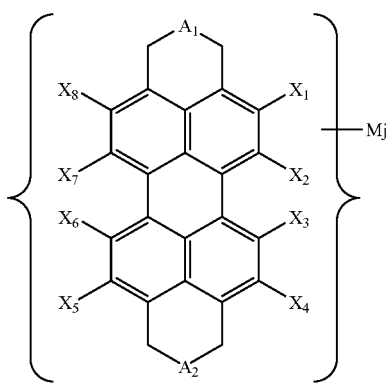

-continued

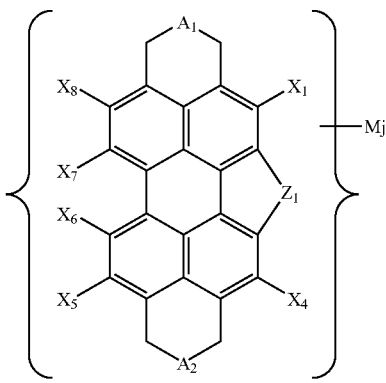

II

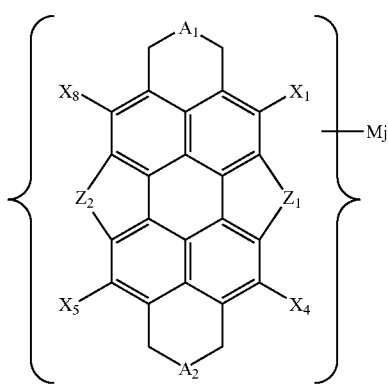

III where $X_1$, $X_2$, $X_3$, $X_4$, $X_5$, $X_6$, $X_7$, and $X_8$ are peripheral substituents individually selected from —H, —OH, and —SO$_3$H, such that at least one of the peripheral substituents is not H;

M is one or more counter ions and j is the number of counter ions associated with a molecule;

$Z_1$ and $Z_2$ are bridging substituents individually selected from —O—, —SO$_2$—, —SO$_2$—O—;

$A_1$ and $A_2$ are fragments having the general structural formula

Y is one or more fragments substituents individually selected from —H, —Cl, —F, —Br, —Alk, —OH, —OAlk, —NO$_2$, and —NH$_2$;

n is an integer selected from 0, 1, and 2; and p is an integer selected from 0, 1, 2, 3, and 4, wherein the film is at least partially crystalline.

20. The optically anisotropic film of claim 19, wherein interplanar spacing in a crystal is in the range of approximately 3.1 Å to 3.7 Å along one of the optical axes.

21. The optically anisotropic film of claim 17, comprising:
a sulfoderivative of structural formula I in a concentration range of approximately 0% to 99% by mass;
a sulfoderivative of structural formula II in a concentration range of approximately 0% to 99% by mass; and
a sulfoderivative of structural formula III in a concentration range of approximately 0% to 50% by mass,
wherein the total amount of formulas I to III is 100% by mass.

22. The optically anisotropic film of claim 17, comprising:
a sulfoderivative of structural formula I in a concentration range of approximately 0% to 50% by mass;
a sulfoderivative of structural formula II in a concentration range of approximately 0% to 70% by mass; and
a sulfoderivative of structural formula III in a concentration range of approximately 0% to 20% by mass,
wherein the total amount of formulas I to III is 100% by mass.

23. The optically anisotropic film of claim 17, further comprising at least one water-soluble organic dye.

24. The optically anisotropic film of claim 17, wherein the film is polarizing.

25. The optically anisotropic film of claim 17, wherein the film is a retarder.

* * * * *